United States Patent
Yoshida et al.

(10) Patent No.: US 8,294,901 B2
(45) Date of Patent: Oct. 23, 2012

(54) OPTICAL TOMOGRAPHY HAVING PATH LENGTH CONTROL BASED ON OBJECT POSITION

(75) Inventors: Hirofumi Yoshida, Yokohama (JP); Norihiko Utsunomiya, Machida (JP)

(73) Assignee: Canon Kabushiki Kaisha, Tokyo (JP)

( * ) Notice: Subject to any disclaimer, the term of this patent is extended or adjusted under 35 U.S.C. 154(b) by 258 days.

(21) Appl. No.: 12/687,421

(22) Filed: Jan. 14, 2010

(65) Prior Publication Data
US 2010/0182612 A1 Jul. 22, 2010

(30) Foreign Application Priority Data
Jan. 22, 2009 (JP) .................. 2009-011615

(51) Int. Cl.
*G01B 11/02* (2006.01)
(52) U.S. Cl. ...................................... 356/497
(58) Field of Classification Search .............. 356/379, 356/397, 479, 497
See application file for complete search history.

(56) References Cited

U.S. PATENT DOCUMENTS

| | | | |
|---|---|---|---|
| 5,512,965 A * | 4/1996 | Snook ............................ | 351/205 |
| 5,870,167 A * | 2/1999 | Knopp et al. .................. | 351/212 |
| 7,480,059 B2 * | 1/2009 | Zhou et al. .................... | 356/498 |
| 7,513,619 B2 * | 4/2009 | Lacombe et al. .............. | 351/205 |
| 7,639,845 B2 | 12/2009 | Utsunomiya | |
| 2005/0070772 A1 * | 3/2005 | Cornsweet .................... | 600/319 |
| 2006/0244972 A1 * | 11/2006 | Fercher ......................... | 356/497 |
| 2007/0076217 A1 * | 4/2007 | Baker et al. ................... | 356/498 |
| 2007/0086011 A1 | 4/2007 | Toida | |
| 2009/0091766 A1 | 4/2009 | Hirose | |
| 2009/0285354 A1 | 11/2009 | Hirose et al. | |
| 2010/0002241 A1 | 1/2010 | Hirose | |
| 2010/0007894 A1 | 1/2010 | Suehira | |
| 2011/0205490 A1 * | 8/2011 | Murata et al. ................. | 351/206 |

FOREIGN PATENT DOCUMENTS
WO WO2008/139799 11/2008

OTHER PUBLICATIONS

Michael Pircher et al.; "Simultaneous SLO/OCT imaging of the human retina with axial eye motion correction"; vol. 15, No. 25 (2007).
U.S. Appl. No. 12/688,118, filed Jan. 15, 2010, Norihiko Utsunomiya.
U.S. Appl. No. 12/603,144, Oct. 21, 2009, Futoshi Hirose, Yasuyuki Numajiri, Shuichi Kobayashi, Kenji Muto, Hirofumi Yoshida.

* cited by examiner

*Primary Examiner* — Hwa Lee
(74) *Attorney, Agent, or Firm* — Fitzpatrick, Cella, Harper & Scinto (57) ABSTRACT

Provided is an optical tomographic imaging apparatus which enables simplification and cost reduction without reducing accuracy when moving part of an object is moved in an optical axis direction of measuring beam. The apparatus using return beam of measuring beam reflected or scattered by an object and reference beam reflected by a reference mirror to image the tomographic image, includes: a reflecting position controlling device for controlling the reflecting position of the reference mirror; a detecting device for a position in a moving part having an optical system for observing the moving part illuminated by an optical system imaging the same on an area sensor based on the Scheimpflug principle and detects position information that the moving part is moved in the direction; and a device for driving the reflecting position controlling device to control the optical path length of the reference beam based on the position information.

16 Claims, 7 Drawing Sheets

OPTICAL TOMOGRAPHY HAVING PATH LENGTH CONTROL BASED ON OBJECT POSITION

BACKGROUND OF THE INVENTION

1. Field of the Invention

The present invention relates to an optical tomographic imaging apparatus. More specifically, the present invention relates to an optical tomographic imaging apparatus used for ophthalmic diagnosis.

2. Description of the Related Art

At present, various ophthalmological apparatuses using optical apparatuses are used. For instance, various optical apparatuses for observing eyes, such as an anterior ocular segment photographing device, a fundus camera, and a scanning laser ophthalmoscope (SLO), are used. In particular, an optical tomographic imaging apparatus by an optical coherence tomography (OCT) using interference phenomenon of multi-wavelength light is an apparatus which can obtain a sample tomographic image at high resolution. The ophthalmological apparatus has become indispensable for out-patient department specializing in retinas. Hereinafter, this apparatus will be referred to as an OCT apparatus.

The OCT apparatus can irradiate measuring beam as low coherent light to a sample and, using an interference system, measure backscattering light from the sample at high sensitivity. In addition, the OCT apparatus can scan the measuring beam on the sample and thereby can obtain a tomographic image at high resolution. For this reason that the OCT apparatus can obtain a tomographic image of a retina in the fundus of an eye to be inspected at high resolution, the OCT apparatus is widely used for ophthalmological diagnosis of retinas. Although, a human eye has involuntary motion of the eye ball, called an involuntary eye movement. Therefore, if the time for the ophthalmological diagnosis of a retina using the OCT apparatus is longer, motion artifacts, which is an irregularity of an image, is caused in the obtained tomographic image of the retina due to the influence of the eye movement.

To prevent motion artifacts, various attempts have hitherto been made. For instance, the document of Christoph K. Hitzenberger, "Simultaneous SLO/OCT imaging of the human retina with axial eye motion correction", Optics Express Vol. 15, No. 25 (2007), discloses a method of using another OCT apparatus in addition to an OCT apparatus for observing fundus. The other OCT apparatus is an apparatus which uses a light source of 1300 nm to obtain a tomographic image of a cornea and monitors the position of the cornea in an optical axis direction (hereinafter, called a vertical direction) of the OCT apparatus for observing fundus. A method has been proposed to control the reference mirror of the OCT for observing fundus for measurement according to the position of the cornea in a vertical direction. The position of the cornea is calculated using the OCT in this manner to reduce motion artifacts to the tomographic image of the retina due to the influence of the eye movement.

As described above, if the measuring time in fundus observation using the OCT apparatus is longer, image irregularity called motion artifacts due to eye movement is caused in the obtained tomographic image of a retina. In the above document, the consideration for reducing motion artifacts is made. However, since the OCT for observing cornea is used together with the OCT for obtaining the tomographic image of the retina, the apparatus becomes larger and the cost of the apparatus is greatly increased.

In view of the above problems, an object of the present invention is to provide an optical tomographic imaging apparatus which enables an apparatus to be simplified and cost thereof to be reduced without reducing accuracy when position information that the moving part of an object is moved in an optical axis direction of measuring beam is detected to reduce the deformation of a tomographic image due to position displacement in the moving part of the object.

SUMMARY OF THE INVENTION

The present invention provides an optical tomographic imaging apparatus configured as follows.

According to the present invention, there is provided an optical tomographic imaging apparatus which splits light from a light source into measuring beam and reference beam, guides the measuring beam to an object, guides the reference beam to a reference mirror, and uses return beam of the measuring beam reflected or scattered by the object and the reference beam reflected by the reference mirror to image the tomographic image of the object, including: a reflecting position controlling device for controlling the reflecting position of the reference mirror; a detecting device for detecting a position in a moving part which has an optical system for observing moving part of the object illuminated by an optical system for illumination with the light from the light source by imaging the same on an area sensor based on the Scheimpflug principle and detects position information that the moving part of the object is moved in an optical axis direction of the measuring beam; and a device for driving the reflecting position controlling device to control the optical path length of the reference beam according to the position information detected by the detecting device for detecting a position in a moving part and reducing the deformation of the tomographic image of the object due to position displacement of the moving part of the object.

Further, according to the present invention, there is provided the optical tomographic imaging apparatus, wherein the object is an eye, the moving part of the object is an anterior ocular segment, and the detecting device for detecting a position in a moving part can detect the positions back and forward the movement of the cornea of the eye in an optical axis direction of the measuring beam.

Further, according to the present invention, there is provided the optical tomographic imaging apparatus, wherein when the depth resolution of the optical tomographic imaging apparatus is Δ, the optical magnification of the optical system for observing moving part is β, and the pitch of the area sensor is p, the following equation is satisfied:

$$\Delta \times \beta > p$$

Further, according to the present invention, there is provided the optical tomographic imaging apparatus, wherein the optical system configured in the optical path of the measuring beam and the optical system for illuminating the moving part of the object in the optical tomographic imaging apparatus are partially shared.

Further, according to the present invention, there is provided the optical tomographic imaging apparatus, wherein the detecting device for detecting a position in a moving part can derive the radius of curvature R of the cornea by illuminating the center position of the eye with a slit beam and calculate the coordinates of the apex of the cornea from the difference between the radius of curvature R and the radius of curvature R' of the cornea derived in the tomographic image of the anterior ocular segment.

Further, according to the present invention, there is provided the optical tomographic imaging apparatus, wherein the detecting device for detecting a position in a moving part can derive the radius of curvature R of the cornea by illuminating the center position of the eye with crossed light of two slit beams and calculate the coordinates of the apex of the cornea from the difference between the radius of curvature R and the radius of curvature R' of the cornea derived in the tomographic image of the anterior ocular segment.

According to the present invention, there can be realized an optical tomographic imaging apparatus which enables apparatus simplification and cost reduction without reducing accuracy when position information that the moving part of an object is moved in an optical axis direction of measuring beam to reduce the deformation of a tomographic image due to position displacement in the moving part of the object.

Further features of the present invention will become apparent from the following description of exemplary embodiments with reference to the attached drawings.

DESCRIPTION OF THE EMBODIMENTS

Preferred embodiments of the present invention will now be described in detail in accordance with the accompanying drawings.

First Embodiment

Figure 1:
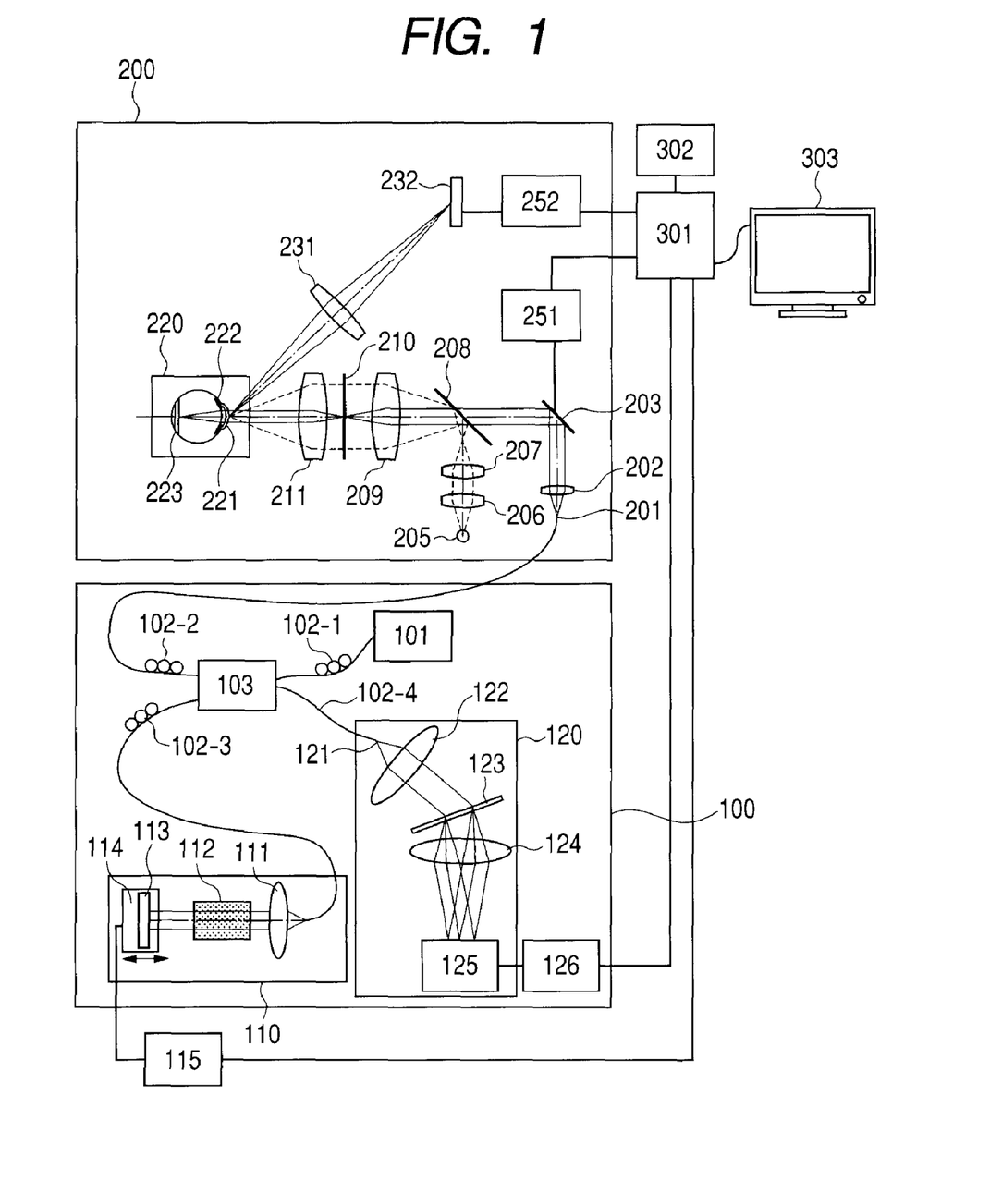
FIG. 1 is a diagram for explaining the configuration of an optical tomographic imaging apparatus measuring system according to a first embodiment of the present invention.

As a first embodiment, a configuration example of an optical tomographic imaging apparatus applied to the present invention will be described. FIG. 1 illustrates a diagram for explaining the configuration of an optical tomographic imaging apparatus measuring system according to the present embodiment. In FIG. 1, the reference numeral 100 denotes an interferometer unit, and the reference numeral 200 denotes a measuring arm. First, the interferometer unit 100 will be described. The optical tomographic imaging apparatus of the present embodiment splits light from a light source into measuring beam and reference beam, guides the measuring beam to an object, guides the reference beam to a reference mirror, and uses return beam of the measuring beam reflected or scattered by the object and the reference beam reflected by the reference mirror to image the tomographic image of the object. Specifically, a low coherence light source emitting a near-infrared ray is used as a light source 101. The light emitted from the light source 101 is propagated through an optical fiber 102-1 and is branched into three optical fibers 102-2, 102-3, and 102-4 by a light branching device 103. The optical fiber 102-2 is connected to the measuring arm 200. The optical fiber 102-3 is connected to a reference beam arm 110. The reference beam arm 110 will be described below. The near-infrared ray emitted from the optical fiber 102-3 enters an optical block 112 via a collimate optical system 111, is reflected by a reflection mirror (reference mirror) 113, and reversely follows the optical path so as to enter the optical fiber 102-3. The optical block 112 compensates the dispersion of the optical system of the measuring arm 200. The reflection mirror 113 is connected to a reflecting position controlling device 114. The reflecting position controlling device 114 controls the reflecting position of the reflection mirror 113. As described later in detail, a device 115 for driving the reflecting position controlling device drives the reflecting position controlling device to control the optical path length of the reference beam according to position information detected by a detecting device for detecting a position in a moving part. This can reduce the deformation of the tomographic image of the object due to position displacement of the moving part of the object.

Next, the measuring arm 200 will be described. In the following description of the embodiment, the case that the object is an eye is taken as an example. The light branched by the light branching device 103 is emitted via the optical fiber 102-2. The light emitted from a fiber end 201 is substantially collimated by an optical system 202. A scanning device 203 is a galvanomirror which can tilt a mirror surface and deflects the incident light. The scanning device 203 is connected to a scanning device controlling circuit 251. In FIG. 1, the scanning device 203 is a two-dimensional scanning device having two galvanomirrors and can perform scanning in a main scanning direction in a sheet surface and a sub-scanning direction in a vertical direction in the sheet surface. The light scanned by the scanning device 203 passes through a beam splitter 208 and forms the conjugate image of the fiber end 201 on an intermediate focusing plane 210 by a focusing lens 209. The light passes through an objective lens 211, an anterior ocular segment 221 and a pupil 222, and forms an illumination spot on a retina 223 of an eye 220 to be inspected. The anterior ocular segment is referred to as the portion from the cornea to the front surface of a crystalline lens of the eye. Upon in-plane deflection of the scanning device 203, the illumination spot is moved on the retina 223. The reflected light in the illumination spot position reversely follows the optical path, enters the fiber end 201, and returns to the light branching device 103.

Light emitted from a light source 205 for observing an anterior ocular segment is transmitted through optical systems 206 and 207 for illuminating an anterior ocular segment, is reflected by the beam splitter 208, and forms an illumination spot on the anterior ocular segment 221 by the focusing lens 209 and the objective lens 211. Here, the optical system configured in the optical path of the measuring beam and the optical system for illuminating the anterior ocular segment in the optical tomographic imaging apparatus are partially shared. The scattered or reflected beams of the illumination spot formed on the anterior ocular segment 221 are focused on an area sensor 232 using an optical system 231 for observing an anterior ocular segment. A tomographic image of the anterior ocular segment is obtained on the area sensor 232. The obtained image is transmitted to an arithmetic operation processing unit 301 via a signal obtaining portion 252. The interference of the light returning from the reference beam arm 110 and the measuring arm 200 is detected by a signal detection arm 120.

The signal detection arm 120 emits the light propagated through the optical fiber 102-4 from the fiber end 121. The light emitted from the fiber end 121 is substantially collimated by an optical system 122. The substantially collimated light enters a diffraction grating 123. The diffraction grating 123 has a period structure and makes the light spectral. The spectral light is focused on a line sensor 125 by a focusing lens 124. The line sensor 125 is connected to a detector controlling device 126 and transmits obtained predetermined data to a storage device 302 via the arithmetic operation processing unit 301. The data of the storage device 302 is Fourier converted by the arithmetic operation processing unit 301 to output a tomographic image of the fundus. The tomographic image is outputted on a display device 303. The present embodiment is a low coherent tomography for fundus using the so-called Fourier domain OCT system. In the present embodiment, there is configured the detecting device for detecting a position in a moving part which has the optical system for observing moving part of the object illuminated by the optical system for illumination with the light from the light source by imaging the same on the area sensor based on the Scheimpflug principle and detects when position information that the moving part of the object is moved in an optical axis direction of the measuring beam. In other words, the detecting device for detecting a position in a moving part can detect the positions of back and forward movement of the cornea of the eye in an optical axis direction of the measuring beam. The position information of the anterior ocular segment is extracted from the tomographic image of the anterior ocular segment. The position of the reflection mirror 113 of the reference beam arm 110 is moved (tracking is performed), whenever necessary, to reduce motion artifacts.

Figure 2A:
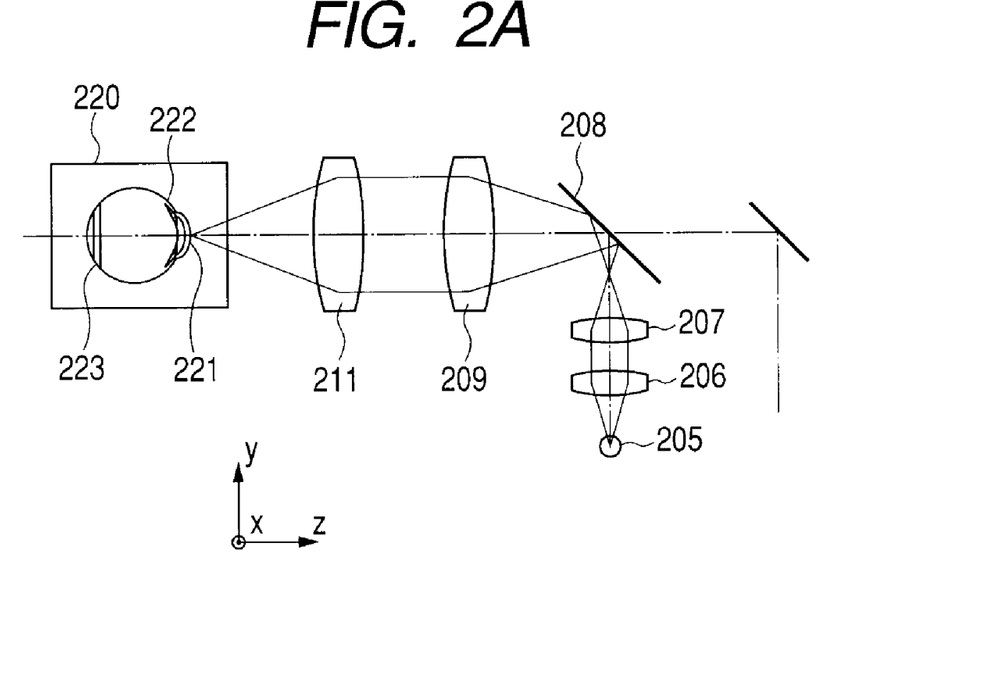
FIGS. 2A and 2B are diagrams for explaining the configurations of an optical system for illuminating an anterior ocular segment and an optical system for observing the anterior ocular segment according to the first embodiment of the present invention.
Figure 2B:
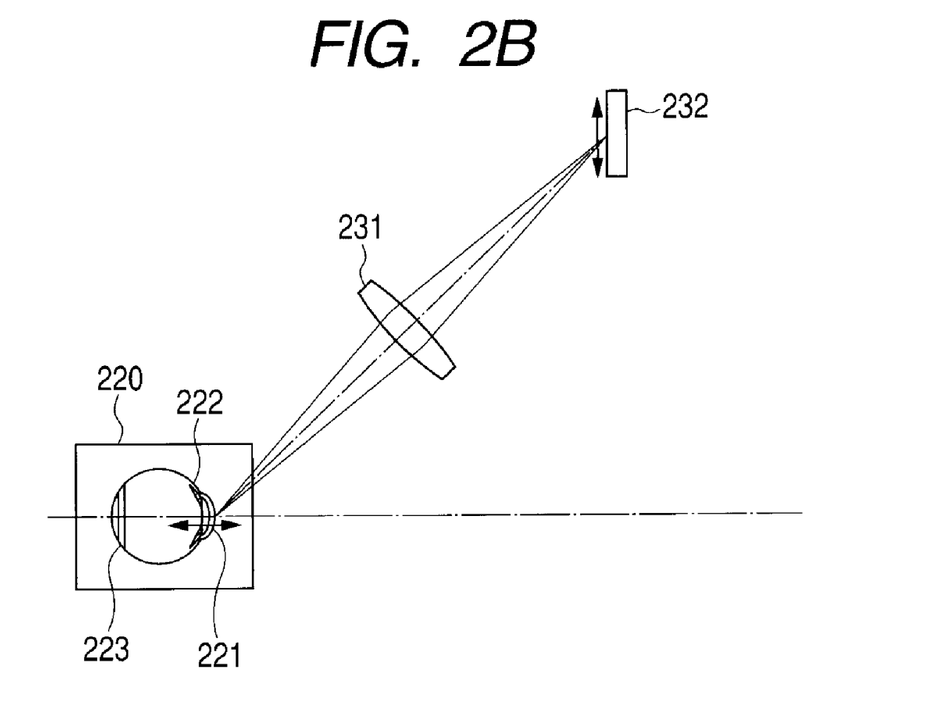

The optical system for illuminating an anterior ocular segment and the optical system for observing an anterior ocular segment (the optical system for observing moving part) will be described below in more detail. FIGS. 2A and 2B illustrate diagrams for explaining the configurations of the optical system for illuminating an anterior ocular segment and the optical system for observing an anterior ocular segment according to the first embodiment of the present invention. FIG. 2A is a diagram for explaining the optical system for illuminating an anterior ocular segment. FIG. 2B is a diagram for explaining the optical system for observing the anterior ocular segment. Hereinafter, the same reference numerals as those illustrated in FIG. 1 have similar functions and description thereof will not be repeated. First, the optical system for illuminating an anterior ocular segment illustrated in FIG. 2A will be described. The light source 205 is a light source having a wavelength of 1300 nm. As the feature of the wavelength range, advantageously, the light is hard to reach the inside of the eye due to high water absorption degree and the anterior ocular segment is easy to be observed. The illuminating light from the light source 205 is transmitted through the optical systems 206 and 207 for illuminating anterior ocular segment and is reflected by the beam splitter 208. The beam splitter 208 has the property of reflecting light having a wavelength of near 1300 nm and of transmitting light having a wavelength of 800 to 900 nm. The observation of the OCT and the illumination of the anterior ocular segment can be coaxially performed. The property of transmission and reflection to the wavelengths may be reverse to the above, in the case, the arrangement of the optical system for illuminating an anterior ocular segment and the optical system for observation of the OCT would also be reverse. The illuminating light reflected by the beam splitter 208 forms an illumination spot on the anterior ocular segment 221 by the focusing lens 209 and the objective lens 211. The depth of focus (DOF) of the illumination spot in a vertical direction is desirably more than eye movement of the eye to be tracked. The anterior ocular segment 221 is illuminated by the above configuration of the optical system.

Next, the optical system for observing an anterior ocular segment illustrated in FIG. 2B will be described. In FIG. 2B, the scattered or reflected beams of the illumination spot formed on the anterior ocular segment 221 by the configuration illustrated in FIG. 2A are focused on the area sensor 232 using the optical system 231 for observing an anterior ocular segment. The optical axis of the optical system 231 for observing an anterior ocular segment is tilted from that of the optical system for illumination. The difference of the position of the eye can be detected as the difference of the position of the image obtained on the area sensor 232. This is typically called Scheimpflug principle. The configuration of the optical system of the present embodiment based on the Scheimpflug principle will be described below.

Figure 3:
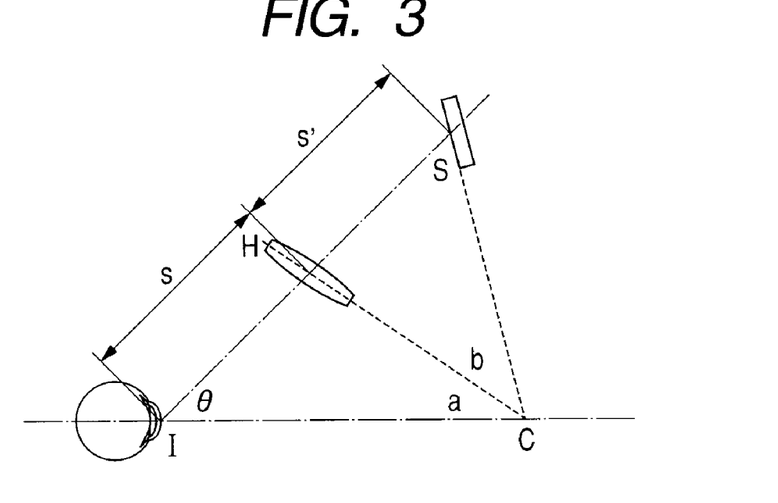
FIG. 3 is a diagram illustrating the optical system based on the Scheimpflug principle according to the first embodiment of the present invention.

FIG. 3 illustrates a diagram illustrating the relation of the optical system. The anterior ocular segment is illuminated by the configuration of FIG. 2A. Of the scattered or reflected beams of the illumination spot from an anterior ocular segment illumination position I, the beam emitted in the direction of an angle θ is detected. When the principal plane of the optical system is H, the anterior ocular segment illumination position I and the principal plane H are separated by a distance of s to arrange the optical system. The optical system is arranged in a manner that, when the cross point of the extension plane of the principal plane H and the optical axis of the illuminating light is C, an angle formed therebetween is a. When the distance between the principal plane H and an area sensor surface S at the angle θ is s' and the focal length of the optical system is f, s' is determined by the following equation:

$$1/s' = 1/s + 1/f$$

A magnification β is s'/s. An angle b formed between the extension plane of the area sensor surface S and the principal plane H is determined so that the extension plane of the area sensor surface S crosses C. As described above, the above configuration can detect the difference of the position of the eye as the difference of the position of the image obtained on the area sensor.

Figure 4A:
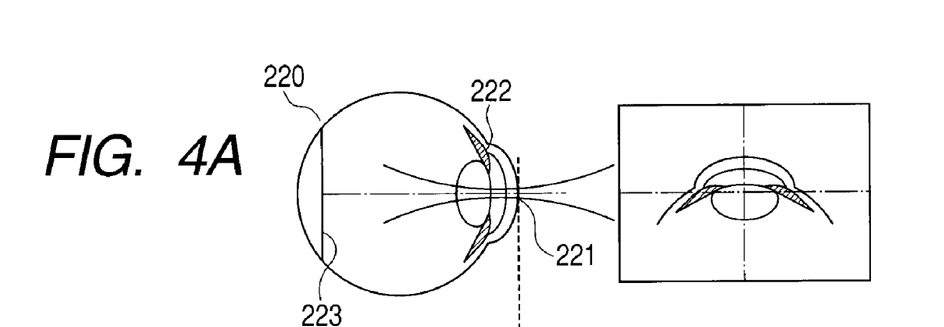
FIGS. 4A, 4B, and 4C are diagrams illustrating tomographic images of the anterior ocular segment obtained on an area sensor according to the first embodiment of the present invention.
Figure 4B:
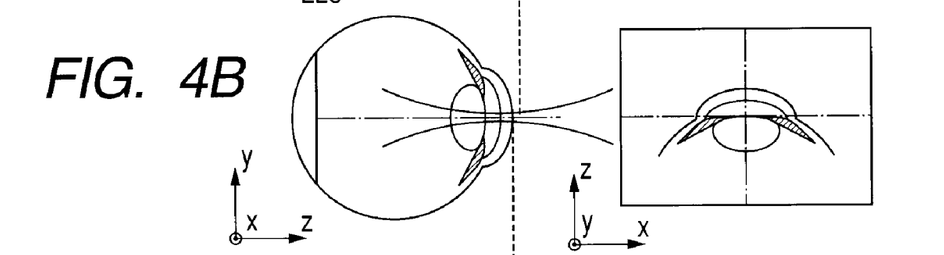
Figure 4C:
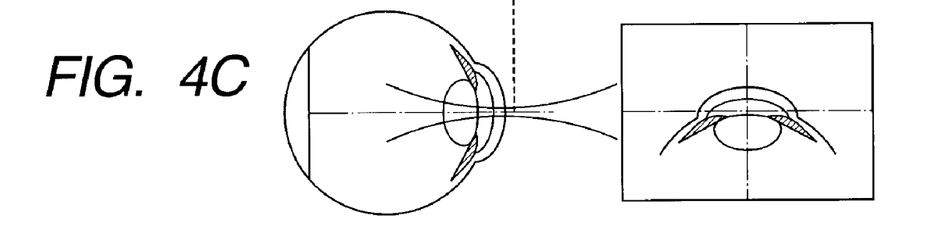

FIGS. 4A to 4C schematically illustrate the tomographic images of the anterior ocular segment obtained on the area sensor 232. In FIGS. 4A to 4C, the positions of the eye are different to one another in an optical axis direction (z direction). In a typical optical system in which the optical axis is coaxial, the difference of the position in the z direction is detected by the area sensor as a defocused image. On the other hand, in the present invention, the axis of optical system 231 for observing an anterior ocular segment is shifted. The difference of the position of the eye is detected as the difference of the position of the image obtained on the area sensor 232. This enables the position detection accuracy in the z direction to be higher than the former method.

The optical axis of the optical system 231 for observing an anterior ocular segment may be bent by a prism, not illustrated, to loosen the incident angle of the light upon the area sensor 232. In addition, when the optical magnification of the optical system 231 for observing an anterior ocular segment is β, the depth resolution of the OCT is Δ, and the pitch of the area sensor is p, the following equation is desirably satisfied:

$$\Delta \times \beta > p$$

This can perform tracking at the depth resolution Δ of the OCT even in consideration of the pitch of the sensor. When the eye is moved outside the range of the depth resolution Δ of the OCT, the movement is detected and the position of the reflection mirror 113 is moved, whenever necessary, to perform tracking.

Here, the depth resolution Δ of the OCT is expressed by the following equation:

$$\Delta = \lambda \times 4 \times f^2 / D^2$$

where λ is the wavelength of the light source, f is the focal length of the eye, and D is the beam diameter incident upon the eye. The tomographic image of the anterior ocular segment is obtained on the area sensor 232. The obtained image is transmitted to the arithmetic operation processing unit 301 via the signal obtaining portion 252. A characteristic point is extracted from the tomographic image of the anterior ocular segment by the arithmetic operation processing unit 301. For instance, interface information between air and the cornea is extracted by binarization processing and determining the differential value of the image to detect the position of the interface on the area sensor. When the position displacement of the interface from the reference position is δz, the discrepancy information of δz is transmitted to the device 115 for driving the point controlling device. The position of the reflection mirror 113 is then moved by δz by the reflecting position controlling device 114 for performing tracking. This is sequentially performed to reduce motion artifacts.

Second Embodiment

In the following, a second embodiment will be described. In the present embodiment, there will be described an example in which the detecting device for detecting a position in a moving part can determine the radius of curvature R of the cornea by illuminating the center position of the eye with a slit beam and calculate the coordinates of the apex of the cornea from the difference between the radius of curvature R and the radius of curvature R' of the cornea determined in the tomographic image of the anterior ocular segment. In other words, in contrast to that the spot illuminates the anterior ocular segment in the first embodiment as illustrated in FIGS. 2A and 2B, in the present embodiment, a configuration example in which the slit beam illuminates the anterior ocular segment will be described. The layout of the interferometer unit 100 is the same as the first embodiment and description thereof will not be repeated.

Figure 5A:
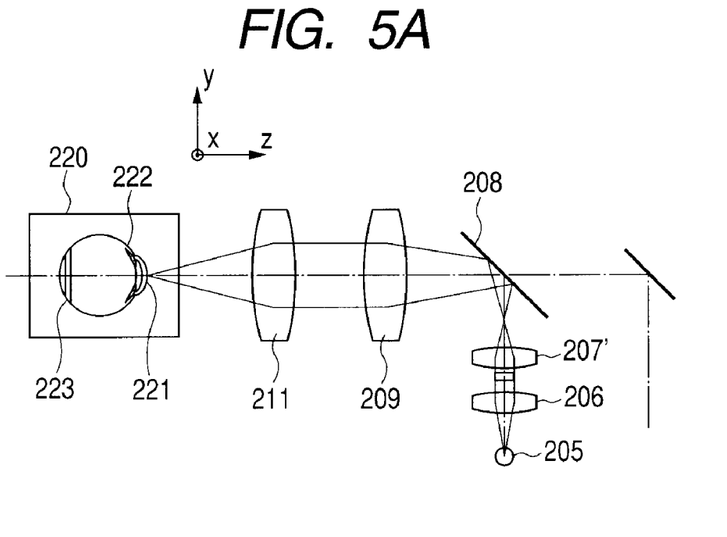
FIGS. 5A, 5B, and 5C are diagrams for explaining the optical system for illuminating an anterior ocular segment according to a second embodiment of the present invention.
Figure 5B:
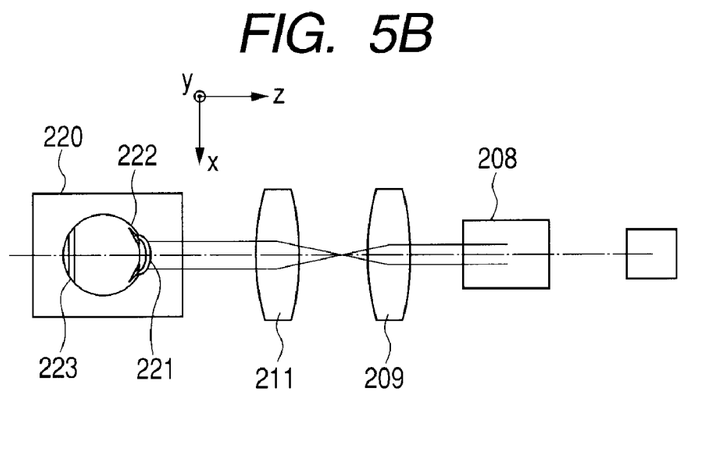
Figure 5C:
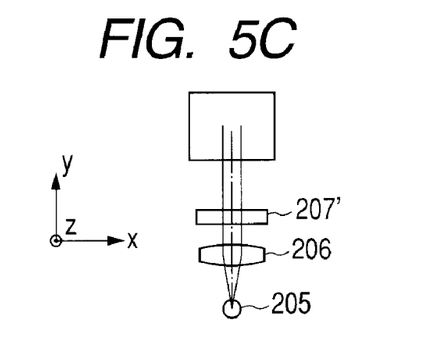
Figure 6:
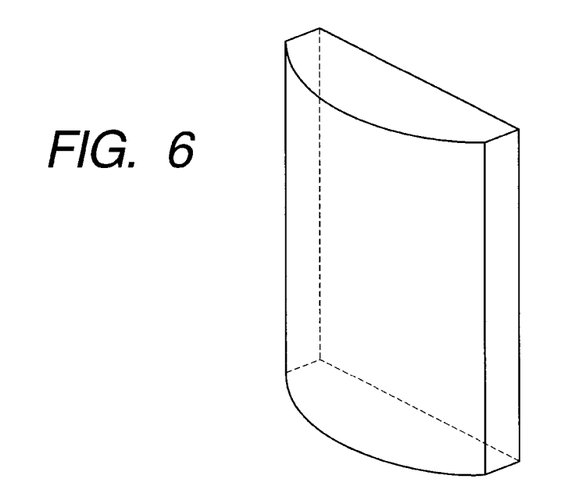
FIG. 6 is a diagram illustrating the shape of a cylindrical lens according to the second embodiment of the present invention.

FIGS. 5A, 5B and 5C illustrate diagrams for explaining the optical system for illuminating anterior ocular segment according to the second embodiment of the present invention. FIGS. 5A, 5B and 5C illustrate an x cross section, a y cross section, and a z cross section, respectively. The illuminating light from the light source 205 is transmitted through the optical system 206 for illuminating anterior ocular segment and enters a cylindrical lens 207'. FIG. 6 illustrates the shape of the cylindrical lens 207'. The cylindrical lens has the property of refracting the light on the x cross section and of not refracting the light on the z cross section. The illuminating light differently refracted based on each cross section is reflected by the beam splitter 208. The illuminating light reflected by the beam splitter 208 illuminates the anterior ocular segment 221 in slit shape by the focusing lens 209 and the objective lens 211. The illuminating light is spot-like seen on the x cross section. The illuminating light is not focused seen on the y cross section and illuminates the wide area. The scattered or reflected beams of the slit illuminating light formed on the anterior ocular segment 221 by the configurations of FIGS. 5A, 5B and 5C are focused on the area sensor 232 using the optical system 231 for observing anterior ocular segment. An optical axis of the optical system 231 for observing an anterior ocular segment is tilted from that of the optical system for illumination. The difference of the position of the eye can be detected as the difference of the position of the image obtained on the area sensor 232 based on the Scheimpflug principle.

Figure 7A:
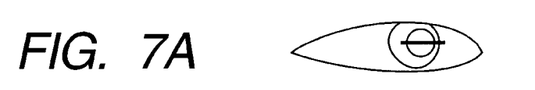
FIGS. 7A, 7B, 7C, 7D, 7E and 7F are diagrams for explaining the differences between the tomographic images of anterior ocular segment due to position displacement between a slit beam and an eye according to the second embodiment of the present invention.
Figure 7B:
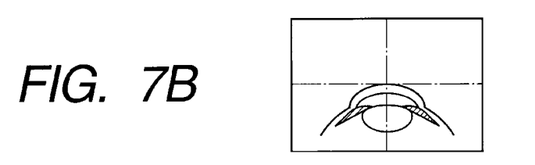

The diagrams for explaining the differences between the tomographic images of the anterior ocular segment due to position displacement between the eye and the slit beam according to the present embodiment are illustrated. FIGS. 7A and 7B schematically illustrate the tomographic image of the anterior ocular segment obtained on the area sensor 232. FIG. 7A illustrates the illuminating state of the slit beam on the anterior ocular segment. FIG. 7B illustrates the tomographic image of the anterior ocular segment obtained on the area sensor 232. Hereinafter, the position of FIGS. 7A and 7B will be called a normal position. The difference of the position of the eye is detected as the difference of the position of the image obtained on the area sensor 232, which is the same as the first embodiment. Like FIGS. 7C and 7D and FIGS. 7E and 7F, when the eye is moved in a horizontal direction (the x or y direction) to the optical system, tracking in the z direction can be performed by taking the shift amount into consideration.

Figure 7C:
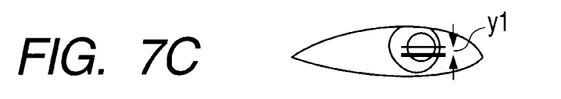
Figure 7D:
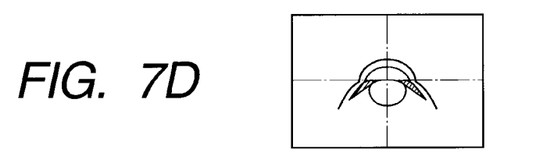

FIGS. 7C and 7D illustrate the case that the eye is moved in the y direction to the optical system. When the eye is moved in the y direction to the slit beam, the plane sectioning the anterior ocular segment is shifted. Therefore, when the anterior ocular segment image of FIGS. 7C and 7D is compared with the anterior ocular segment image detected in the normal position of FIGS. 7A and 7B, the curvatures of the cornea are different. Then, the difference of the curvature of the cornea can be used to calculate the amount of movement in the y direction so that the top position can be determined. The procedure will be described below. The radius of curvature of the cornea herein is the approximate curvature of the cornea determined by the tomographic image of the anterior ocular segment. The radius of curvature of the cornea can be determined by determining the position coordinates of the cornea on at least three points and by fitting using the least squares method.

First, the radius of curvature of the cornea is measured. The anterior ocular segment image is imaged on the area sensor 232 using the optical system 231 for observing an anterior ocular segment in the position where the slit beam illuminates the center position of the eye, and the radius of curvature is determined from the image. Alternately, if the center position is ambiguous, the light source 205 is shifted in a vertical direction to the optical axis and the above operation of determining the radius of curvature is performed for each shift, and the light source 205 is set in the position where the radius of curvature is maximum, so that the radius of curvature of the cornea can also be measured. When the cornea is assumed to be spherical and the coordinates of the apex of the cornea in the normal position are (x, y, z)=(0, 0, 0), the shape of the cornea can be expressed by the following equation:

$$x^2 + y^2 + (z - R - z1)^2 = R^2 \quad \text{Equation (1)}$$

where R is the radius of curvature of the cornea, and z1 is the amount of movement of the eye in the z direction. In the normal position of FIGS. 7A and 7B, the anterior ocular segment is sectioned at y=0. Then, Equation (1) becomes $$x^2+(z-R-z1)^2=R^2 \qquad \text{Equation (2)}$$

The relation is imaged on the area sensor 232. Therefore, tracking in the z direction can be performed by reading z1. On the other hand, when the optical axis is shifted by y1 in the y direction like FIGS. 7C and 7D, the anterior ocular segment is sectioned at y=y1. Then, Equation (1) becomes $$x^2+(z-R-z1)^2=R^2-y1^2=R'^2 \qquad \text{Equation (3)}$$

The radius of curvature of the image on the area sensor 232 becomes $R'=\sqrt{(R^2-y1^2)}$.

the amount of movement $y1^2$ in the y direction from the normal position can be determined by using the radius of curvature calculated from the image on the area sensor 232 and the first measured radius of curvature R of the cornea. However, as understood from $y1^2$ in the equation, here, it cannot be found whether y1 is a positive value or a negative value. However, a plurality of slit beams can be incident upon the eye so that the absolute value of y1 is found. From the above description, in consideration of the amount of movement y1 in the y direction, z1 is calculated so that tracking in the z direction can be performed.

Figure 7E:
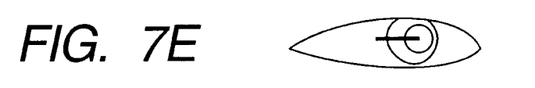
Figure 7F:
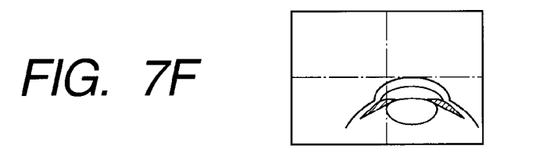

FIGS. 7E and 7F illustrate the case that the eye is moved in the x direction to the optical system. When the eye is moved in the x direction to the slit beam, the image is shifted in the x direction in the area sensor 232 so that the amount of movement in the x direction can be calculated from the image position. In addition, the amounts of movement in the x direction and the y direction can be independently determined. Therefore, even when the eye is moved in both the directions, the coordinates of the apex of the cornea are calculated so that tracking in the z direction can be performed. Further, even when the eye is rotated relative to the optical system, tracking in the z direction can be performed by taking the shift amount into consideration.

Figure 8A:
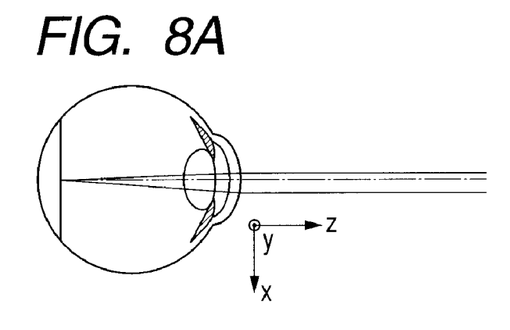
FIGS. 8A, 8B, 8C, 8D, 8E and 8F are diagrams for explaining the differences between the tomographic images of anterior ocular segment and tomographic images of fundus, due to position displacement between illuminating light and an eye and rotation of the eye according to the second embodiment of the present invention.
Figure 8B:
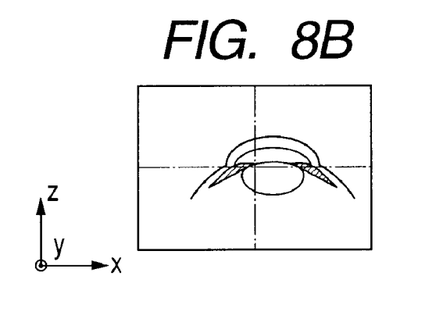
Figure 8C:
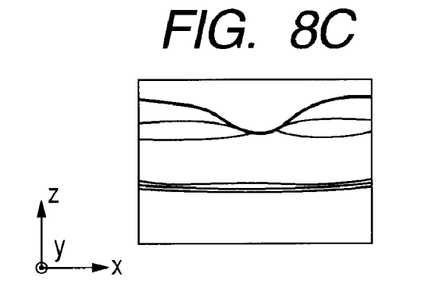
Figure 8D:
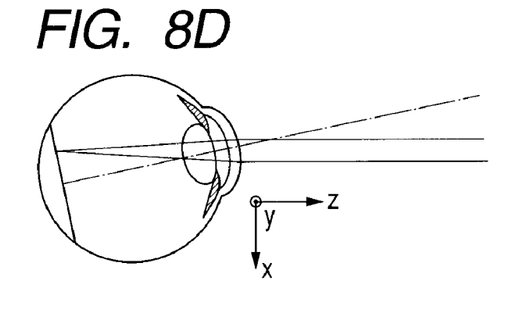
Figure 8E:
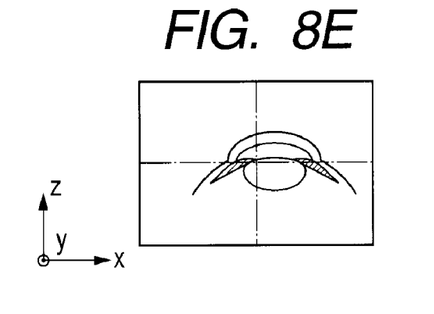
Figure 8F:
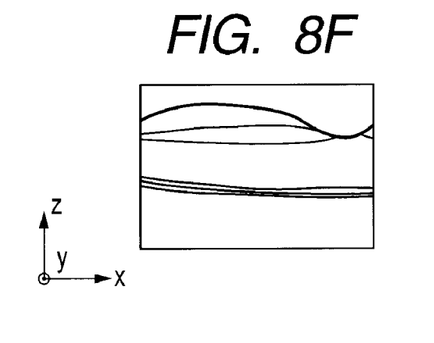

FIGS. 8A, 8B, 8C, 8D, 8E and 8F illustrate diagrams for explaining the differences between the tomographic images of the anterior ocular segment and the tomographic images of the fundus due to position displacement between the illuminating light and the eye and rotation of the eye according to the present embodiment. FIGS. 8A, 8B and 8C illustrate that the eye is shifted in the y direction to the optical system and FIGS. 8D, 8E and 8F illustrate that the eye is rotated in the y direction. FIGS. 8A and 8D illustrate the optical paths of the illuminating light on the fundus. FIGS. 8B and 8E illustrate the tomographic images of the anterior ocular segment. FIGS. 8C and 8F illustrate the tomographic images of the fundus. Comparing the image when the eye is shifted with the image when the eye is rotated, the illuminated area of the anterior ocular segment, not illustrated, is hardly changed in the tomographic image of the anterior ocular segment, but the illuminated area of the fundus is largely changed in the tomographic image of the fundus. This is because, whereas in shifting of the eye, almost the same position of the illuminated area of the fundus is illuminated, by contrast in the rotation of the eye, the beam with the angle of view enters the eye to shift the illuminated area of the fundus. Then, tracking in the z direction can be performed by detecting the shift of the illuminated area of the fundus, and calculate a rotation angle which is converted to an optical path length. The correspondence of the conversion of the rotation angle to the optical path length need be performed in advance.

Third Embodiment

Figure 9A:
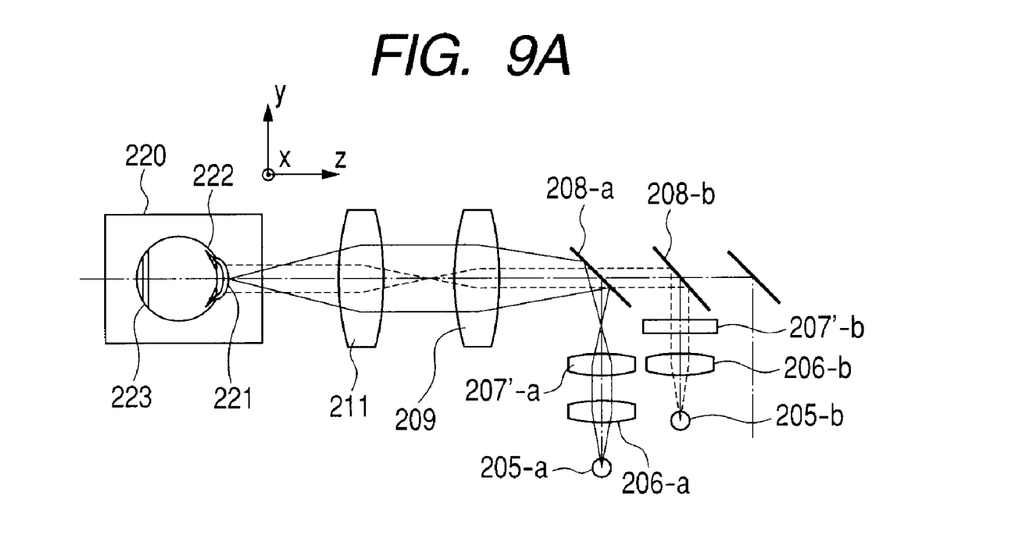
FIGS. 9A, 9B and 9C are diagrams for explaining the optical system for illumination with crossed light according to a third embodiment of the present invention.
Figure 9B:
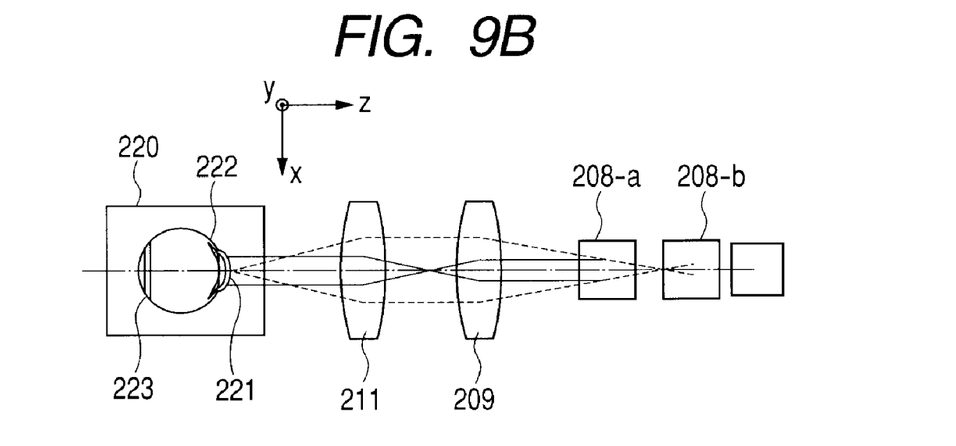
Figure 9C:
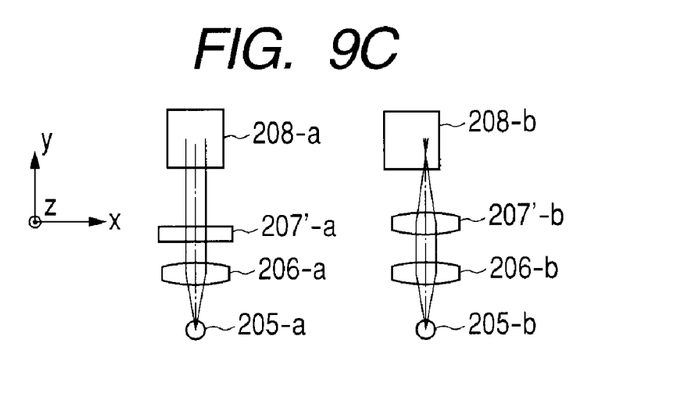

A third embodiment will be described. In the present embodiment, there will be described an example in which the detecting device for detecting a position in a moving part can determine the radius of curvature R of the cornea by illuminating the center position of the eye with crossed light of two slit beams and calculate the coordinates of the apex of the cornea from the difference between the radius of curvature R and the radius of curvature R' of the cornea determined in the tomographic image of the anterior ocular segment. In other words, in the present embodiment, there will be described a configuration example in which the slit beams cross each other (hereinafter, called crossed light) for illumination will be described. The layout of the interferometer unit 100 is the same as the first embodiment and description thereof will not be repeated. FIGS. 9A, 9B and 9C illustrate diagrams for explaining the optical system for illumination with the crossed light according to the present embodiment. FIG. 9A illustrates the x cross section, FIG. 9B illustrates the y cross section, FIG. 9C illustrates the z cross section. The light source 205-*a* is used for the slit beam extended in the x-axis direction. The light source 205-*b* is used for the slit beam extended in the y-axis direction. The optical systems 206-*a*, 207'-*a*, 208-*a*, 209, and 211 for the slit beam extended in the x-axis direction are the same as FIGS. 5A, 5B and 5C and description thereof will not be repeated.

The optical system for the slit beam extended in the y-axis direction will be described. The optical paths indicated by the dashed lines of FIGS. 9A to 9C are optical paths of the slit beam extended in the y-axis direction. The illuminating light from the light source 205-*b* is transmitted through the optical system 206-*b* for illuminating an anterior ocular segment and enters the cylindrical lens 207'-*b*. The cylindrical lens 207'-*a* has the property of not refracting the light on the x cross section and of refracting the light on the z cross section. The illuminating light differently refracted based on each cross section is reflected by the beam splitter 208-*b*. The illuminating light reflected by the beam splitter 208 illuminates the anterior ocular segment 221 in slit shape by the focusing lens 209 and the objective lens 211. The illuminating light is not focused seen on the x cross section and illuminates the wide area. On the other hands, the illuminating light is illuminating spot-likely seen on the y cross section. In other words, the illuminating light is the slit beam extended in the y-axis direction.

The scattered or reflected beams of the cross illuminating light formed on the anterior ocular segment 221 by the configurations of FIGS. 9A, 9B and 9C are focused on the area sensor using the optical system for observing an anterior ocular segment. At least two area sensors are necessary using the optical system for observing an anterior ocular segment. The directions to which the optical axes are tilted need be vertical to each other. The area sensor is also provided in a vertical direction in the sheet surface using the optical system for observing an anterior ocular segment illustrated in FIG. 2B. The optical system for observing an anterior ocular segment shifted in the y direction and the area sensor focus the scattered or reflected beams of the illuminating light extended in the x direction, of the crossed light illustrated in FIG. 9. The optical system for observing an anterior ocular segment shifted in the x direction and the area sensor focus the scattered or reflected beams of the illuminating light extended in the y direction, of the crossed light illustrated in FIG. 9.

The method of extracting the coordinates of the apex of the cornea is the same as the second embodiment and description thereof will not be repeated. By the above configuration, the tomographic image of the anterior ocular segment can be obtained on each of the x cross section and the y cross section. The accuracy is increased because the amounts of movement in the x direction and the y direction are determined both from two directions. In addition, the coordinates of the apex of the cornea can be extracted even if the shape of the cornea is asymmetrical. The crossed light having different wavelengths may be emitted. The light sources 205-a and 205-b may be light sources having different wavelengths to obtain the tomographic image of the anterior ocular segment.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-011615, filed Jan. 22, 2009, which is hereby incorporated by reference herein in its entirety.

What is claimed is:

1. An optical tomographic imaging apparatus which splits light from a light source into a measuring beam and a reference beam, guides the measuring beam to an object, and acquires a tomographic image of the object based on a combined beam of a return beam of the measuring beam reflected or scattered by the object and the reference beam, comprising:
a detecting unit configured to detect light emitted at a predetermined angle to an optical path of the measuring beam;
an obtaining unit configured to obtain a position of the object in an optical axis direction of the optical path of the measuring beam, based on a result of the detection; and
a control unit configured to change an optical path length of the reference beam based on the position of the object in the optical axis direction.

2. The optical tomographic imaging apparatus according to claim 1, further comprising a lens and a sensor arranged on an optical path toward the predetermined angle and at a position determined based on the Scheimpflug principle, wherein
the object is an eye, and said detecting unit is configured to detect the positions of back and forward movement of a cornea of the eye in an optical axis direction.

3. The optical tomographic imaging apparatus according to claim 1, wherein said detecting unit comprises an optical system and an area sensor, and
wherein when a depth resolution of said optical tomographic imaging apparatus is $\Delta$, an optical magnification of said observing optical system that observes the object is $\beta$, and a pitch of said area sensor is p, the following equation is satisfied:

$$\Delta \times \beta > p.$$

4. The optical tomographic imaging apparatus according to claim 2, wherein said detecting unit is configured to detect the position of the eye to derive a radius of curvature R of the cornea by illuminating a center position of the eye with a slit beam,
said optical tomographic imaging apparatus further comprising a calculating unit configured to calculate coordinates of an apex of the cornea from a difference between the radius of curvature R and a radius of curvature R' of the cornea derived in said tomographic image of an anterior ocular segment of the eye.

5. The optical tomographic imaging apparatus according to claim 2, wherein said detecting unit is configured to detect the position of the eye to derive a radius of curvature R of the cornea by illuminating a center position of the eye with crossed light of two slit beams,
said optical tomographic imaging apparatus further comprising a calculating unit configured to calculate coordinates of an apex of the cornea from a difference between the radius of curvature R and a radius of curvature R' of the cornea derived in said tomographic image of an anterior ocular segment of the eye.

6. The optical tomographic imaging apparatus according to claim 1, further comprising a reflecting position controlling unit configured to control a reflecting position of a reference mirror, wherein
said control unit is further configured to control the reflecting position controlling unit based on the position of the object in an optical axis direction.

7. A method for controlling an optical tomographic imaging apparatus which acquires a tomographic image of an object based on a combined beam of a return beam from the object to which a first measuring beam is irradiated and a first reference beam corresponding to the first measuring beam, comprising:
detecting, on an optical axis that is different from an optical axis of the first measuring beam, a return beam from the object to which a second measuring beam having a different wavelength from the first measuring beam is irradiated, wherein at least a part of an optical system of the second measuring beam shares at least a part of an optical system of the first measuring beam; and
changing an amount of difference between the beam path lengths of the reference beam and the measuring beam, based on a result of the detection.

8. The method for controlling an optical tomographic imaging apparatus according to claim 7, wherein
object is an eye, and
the method further comprises steps of:
obtaining a tomographic image of a cornea of the eye, based on a result of the detection, wherein the amount of difference of the beam path lengths is changed based on a predetermined position in the tomographic image of a cornea, so as to reduce deformation of the tomographic image of the object caused by a positional misplacement of the object.

9. A non-transitory computer readable medium in which a program for executing each step of the method of claim 7 in a computer is recorded.

10. An optical tomographic imaging apparatus, in which a tomographic image of an object is obtained based on a combined beam of a return beam from the object to which a first measuring beam is irradiated and a first reference beam corresponding to the first measuring beam, comprising:
a beam path length changing unit configured to change an amount of difference between beam path lengths of the reference beam and the measuring beam;
a detecting unit, provided on an optical axis that is different from an optical axis of the first measuring beam, configured to detect a return beam from the object to which a second measuring beam, having a different wavelength from the first measuring beam, is irradiated, wherein at least a part of an optical system of the second measuring beam shares at least a part of an optical system of the first measuring beam; and
a control unit configured to control the beam path length changing unit, based on a result of the detection by the detecting unit.

11. The optical tomographic imaging apparatus according to claim 10, wherein the control unit is configured to control the beam path length changing unit so as to reduce deformation of the tomographic image of the object caused by a positional misplacement of the object.

12. The optical tomographic imaging apparatus according to claim 10, further comprising:
   a scanning unit configured to scan the first measuring beam on the object,
   a first optical member configured to irradiate the first and second measuring beams on the object, and
   a second optical member, provided between the scanning unit and the first optical member, which is configured to transmit one of the first and second measuring beams and to reflect the other.

13. The optical tomographic imaging apparatus according to claim 10, wherein
   the object is an eye, and
   the apparatus further comprises:
   a unit configured to obtain a tomographic image of a cornea of the eye, based on a result of the detection, wherein the control unit is configured to control the beam path length changing unit based on a predetermined position in the tomographic image of a cornea.

14. The optical tomographic imaging apparatus according to claim 13, further comprising:
   a calculating unit configured to calculate an amount of movement of the eye in a direction of an optical axis of the first measuring beam, based on a radius of curvature of the cornea in the tomographic image of the cornea and the predetermined position in the tomographic image of a cornea.

15. The optical tomographic imaging apparatus according to claim 14, wherein the calculating unit is configured to calculate a rotation angle of the eye with respect to the optical axis of the first measuring beam, based on a positional displacement of a fundus in a tomographic image of the fundus, and to calculate an amount of movement of the eye in a direction of an optical axis of the first measuring beam, based on the rotation angle, the radius of curvature of the cornea, and the predetermined position in the tomographic image of a cornea.

16. The optical tomographic imaging apparatus according to claim 10, wherein positions of the optical axis of the first measuring beam and the detecting unit are determined based on the Scheimpflug principle.

\* \* \* \* \*